United States Patent
Davey et al.

(10) Patent No.: US 7,521,483 B2
(45) Date of Patent: Apr. 21, 2009

(54) COPRODUCTION OF METHANOL AND AMMONIA FROM NATURAL GAS

(75) Inventors: William Davey, Frankfurt am Main (DE); Thomas Wurzel, Oberursel (DE)

(73) Assignee: Lurgi AG, Frankfurt am Main (DE)

( * ) Notice: Subject to any disclaimer, the term of this patent is extended or adjusted under 35 U.S.C. 154(b) by 0 days.

(21) Appl. No.: 10/593,925

(22) PCT Filed: Feb. 10, 2005

(86) PCT No.: PCT/EP2005/001330

§ 371 (c)(1), (2), (4) Date: Jul. 30, 2007

(87) PCT Pub. No.: WO2005/095313

PCT Pub. Date: Oct. 13, 2005

(65) Prior Publication Data

US 2007/0299144 A1  Dec. 27, 2007

(30) Foreign Application Priority Data

Mar. 22, 2004  (DE) ........................ 10 2004 014 292

(51) Int. Cl.
*C07C 27/14* (2006.01)
(52) U.S. Cl. ........................ 518/703; 423/359; 423/237
(58) Field of Classification Search .................. 423/359, 423/237; 518/703
See application file for complete search history.

(56) References Cited

U.S. PATENT DOCUMENTS

| 6,248,794 | B1 * | 6/2001 | Gieskes ...................... 518/700 |
| 6,599,491 | B2 * | 7/2003 | Vidalin ....................... 423/359 |
| 7,183,326 | B2 * | 2/2007 | Davey et al. ................ 518/700 |

* cited by examiner

*Primary Examiner*—Daniel M Sullivan
*Assistant Examiner*—Sudhakar Katakam
(74) *Attorney, Agent, or Firm*—Andrew Wilford

(57) ABSTRACT

The invention relates to a method for the coproduction of methanol and ammonia from natural gas involving the following steps: 1. Natural gas (flow 1), steam and oxygen are mixed with one another in a reactor A during which the natural gas is partially oxidized and additionally reformed with the aid of catalysts; 2. The gas mixture removed from reactor A is split into a flow (flow 2) for synthesizing methanol in a unit E and into another flow (flow 3) for producing hydrogen; 3. The carbon monoxide present in flow (flow 3) for producing hydrogen is converted into carbon dioxide inside reactor B with the aid of catalysts and intermediate cooling stages; 4. Remaining impurities such as methane, traces of carbon monoxide and argon are washed out in a cleaning unit D, and hydrogen (flows 6, 8) is fed to the methanol synthesis in unit E and to the ammonia synthesis in unit F; 5. The methanol synthesis gas (flow 7) is converted into methanol (flow 9) with the aid of a catalyst, and the methanol is brought to the required level of purity by distillation; 6. The ammonia synthesis gas,(flow 8) is compressed in unit F and converted into ammonia (flow 10) with the aid of a catalyst, and the ammonia is separated from the recovered synthesis gas by partial condensation.

18 Claims, 3 Drawing Sheets

COPRODUCTION OF METHANOL AND AMMONIA FROM NATURAL GAS

CROSS REFERENCE TO RELATED APPLICATIONS

Figure 1:
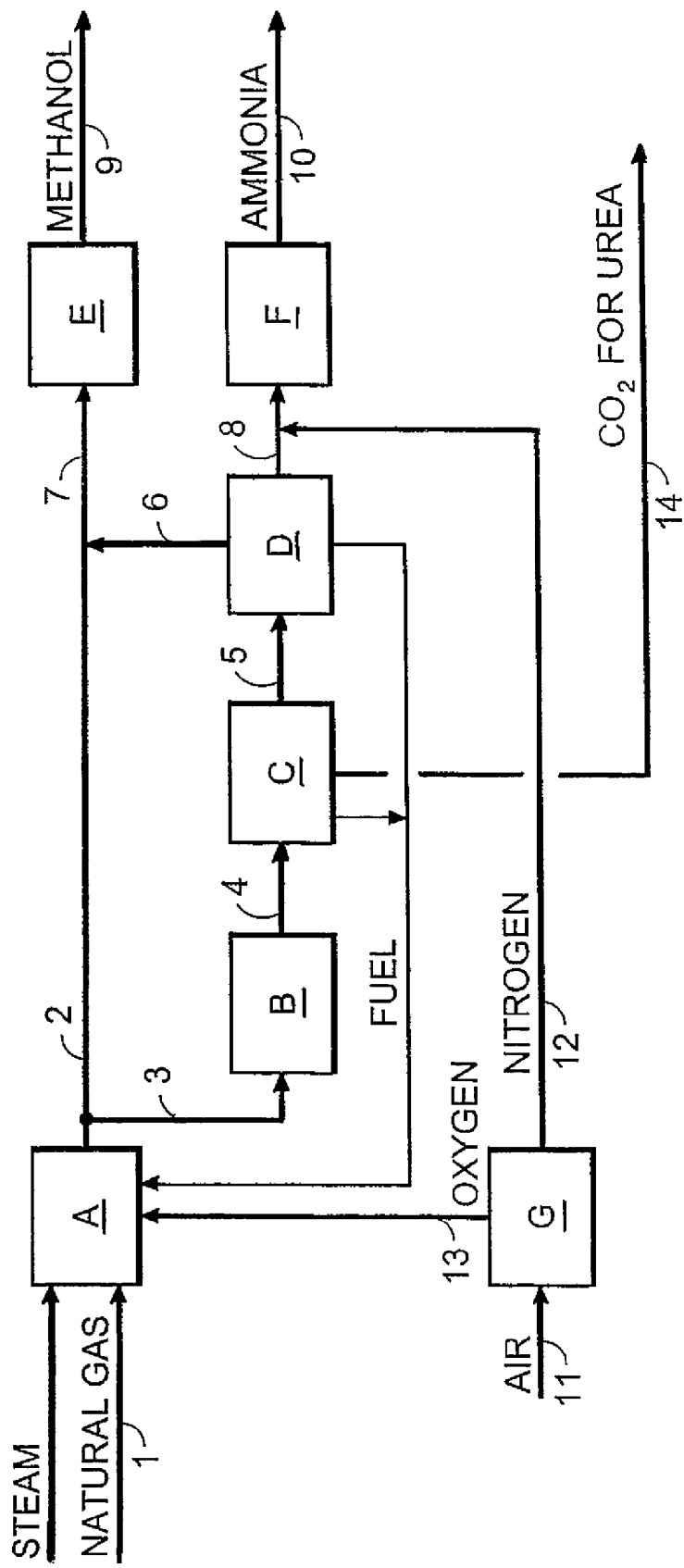

This application is the US national phase of PCT application PCT/EP2005/001330, filed 10 Feb. 2005, published 13Oct. 2005 as WO 2005/095313, and claiming the priority of German patent application 102004014292.0 itself filed 22 Mar. 2004.

The invention relates to a method for the coproduction, that is the simultaneous generation of methanol and ammonia from natural gas, in a single unbroken process sequence.

It is a widespread practice to develop and construct separate processes for the industrial production of methanol and ammonia and to manufacture one of these products at a time. From an economic viewpoint it is however advantageous to manufacture methanol as well as ammonia in a single process sequence, because by that the costs in comparison to separate process sequences for each product are decreased considerably. The costs will be lowered not only for carrying out the manufacturing method, but also already by smaller purchases of equipment sites required for manufacturing the plant.

The integration of methanol manufacture and ammonia manufacture into a single method has been known a long time, compare concerning this for example U.S. Pat. No. 3,598,527. The syntheses of methanol and ammonia take place in tandem, and the purification gas from the first synthesis carried out is fed to the synthesis downstream. Compared with this a method is known from German Patent 696 08 301 with two separate processes for production of methanol and ammonia, the steam reformer in the production of methanol obtaining its energy from the production of ammonia.

All these methods have the disadvantage that the synthesis of methanol and the syntheses of methanol and ammonia are not carried out simultaneously and independently of each other from a single synthesis gas stream.

From German Patent 102 26 209 the decomposition of a synthesis gas is known, methanol synthesis gas, ammonia synthesis gas, carbon monoxide and carbon dioxide being produced.

The object of the present invention is to make available a method by which methanol and ammonia are manufactured in a single integrated process.

With the method in accordance with the invention 5,000 metric tons of methanol can for example be produced per day. The synthesis of methanol requires for this a synthesis gas composition with a stoichiometric number of 2.05 and a carbon dioxide concentration in the range between 2% and 3%. The stoichiometric number $S_n$ is calculated by the following formula:

$$S_n = ([H_2]-[CO_2])/([CO_2]+[CO])$$

Here the magnitudes $[H_2]$, $[CO_2]$, and $[CO]$ stand for the mole fractions of hydrogen, carbon dioxide and carbon monoxide as they are in each case present in the synthesis gas.

Additionally, 4,000 metric tons of ammonia can be produced per day for example by the method in accordance with the invention. A part of this can be used for the manufacture of urea. For the synthesis of ammonia a mixture of hydrogen and nitrogen in the mole ratio of 3:1 is needed having less than 10 ppm in ingredients in which oxygen is contained.

Furthermore, 6,800 metric tons per day of urea can for example be produced. The synthesis of urea requires pure ammonia and carbon dioxide with a purity of more than 98.5%.

These requirements are fulfilled by the following procedure:

From natural gas (stream 1), raw synthesis gas (streams 2 and 3) is produced in reactor A at a pressure of about 40 bar.

The raw synthesis gas from reactor A is split up into a stream for methanol synthesis (stream 2) and into a stream to the carbon monoxide conversion reactor in the reactor B (stream 3). The splitting up is carried out in a ratio such that more gas is fed to reactor B than is used for the synthesis of methanol.

The cooled and condensed gas (stream 4) is if necessary compressed in the compressor and absorber C and fed to a carbon dioxide absorption column. The carbon dioxide-free gas is fed to a purification unit D (stream 5), the recovered carbon dioxide is branched off for the urea synthesis (stream 14) and remaining impurities are fed to the fuel system. The remainder of the gas is treated in a fine wash section of the absorption columns, so as to achieve a carbon dioxide concentration of less than 10 ppm, and likewise is subsequently fed to the purification unit D (stream 5).

Remaining impurities in the gas are removed in the purification unit D by variable pressure absorption with molecular sieves. The hydrogen produced thereby is split up into two streams. One stream (stream 6) is fed to the methanol synthesis gas stream (stream 7), in order to bring about the correct stoichiometry of 2.05, and the second stream is mixed with nitrogen from the air separation unit G (stream 12), in order to obtain ammonia synthesis gas (stream 8) for unit F. Impurities in the form of methane, argon and carbon monoxide are fed to the fuel system to serve as fuel for the process ovens.

In units E and F the methanol synthesis gas stream and the ammonia synthesis gas stream (streams 7 and 8) are converted respectively into methanol (stream 9) and ammonia (stream 10). The methanol is purified by distillation in unit E, and in unit F pure ammonia is produced which makes any further purification unnecessary.

As already mentioned above, the carbon dioxide for the urea synthesis is produced from the compressor and absorber C (stream 14).

BREIF DESCRIPTION OF THE DRAWING

Figure 2:
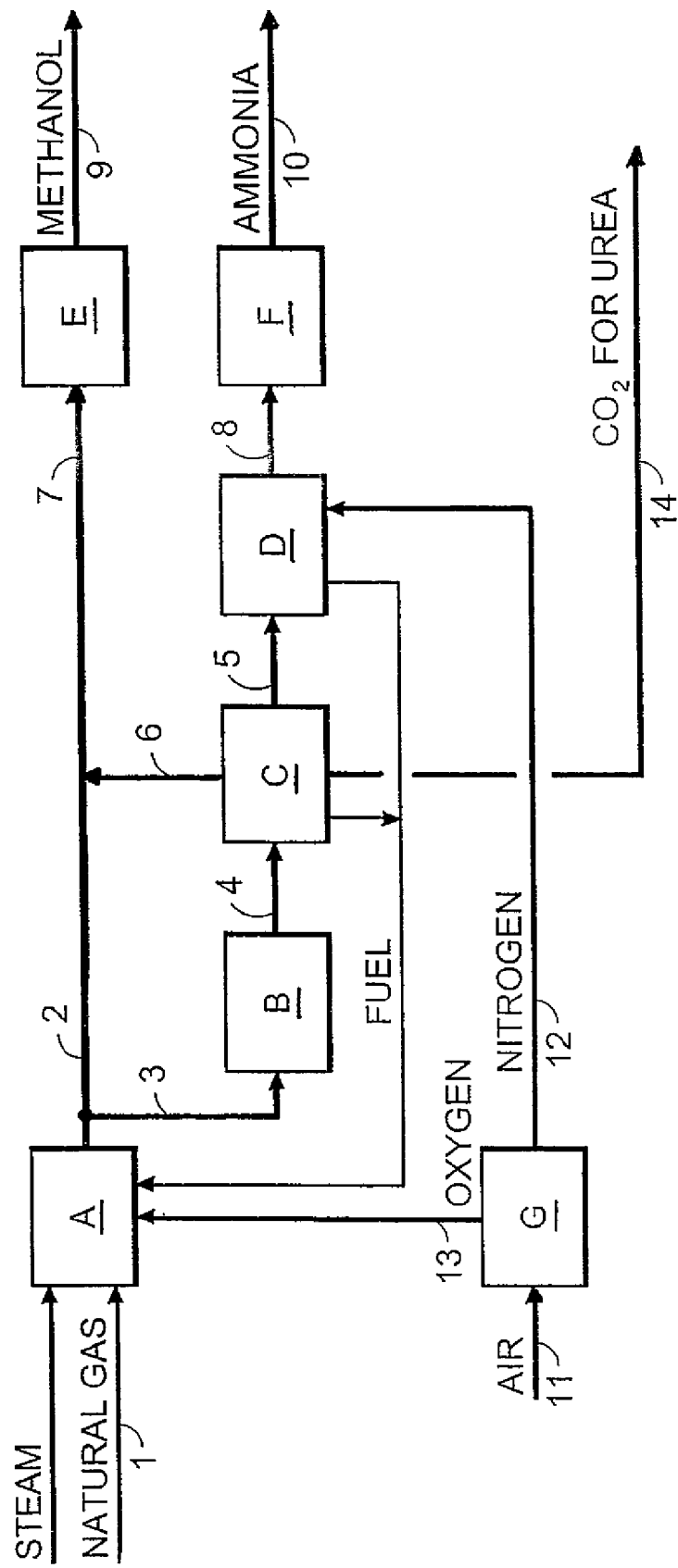
Figure 3:
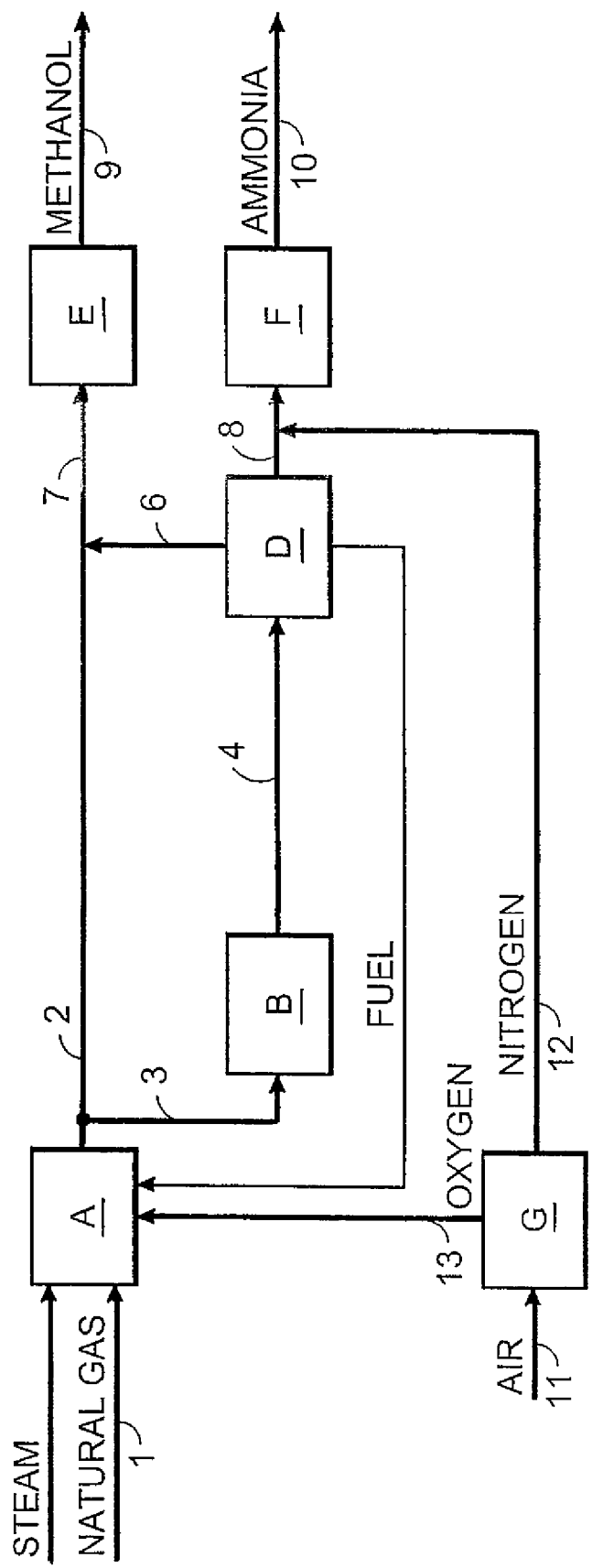

The invention is explained below based on the figures which show,

FIG. 1 An arrangement for the coproduction of methanol and ammonia from natural gas, corresponding to the method described above, FIG. 2 An arrangement for the coproduction of methanol and ammonia, there being in the purification unit D washing with liquid nitrogen from the air separation unit G (stream 12). In this case the hydrogen (stream 6) fed to the methanol synthesis gas is already taken from the compressor and absorber C, FIG. 3 An arrangement for the coproduction of methanol and ammonia, the compressor and absorber C being eliminated entirely, and the purification unit D includes variable pressure absorption. In this case no carbon dioxide is diverted for the urea synthesis.

The production of synthesis gas takes place in reactor A. A few or all of the following individual steps can be contained therein: desulfurization of the natural gas, dampening up to saturation with water vapor, preheating in an oven, pre-reforming, catalytic partial oxidation with oxygen from an air separation unit, as well as gas cooling in a waste heat boiler for the increased generation of steam. The CPOX (Catalytic Partial Oxidation) reactor employed for that is itself a conventional cylindrical vessel with concave, vertically arranged boundary surfaces. A burner or mixer is attached at the top end of the vessel through which the natural gas is mixed with steam. Steam and oxygen are fed into the vessel through separate lines. The oxygen can for example be obtained from the air separation unit G, in which by low temperature distillation the components oxygen (stream 13) and nitrogen (stream 12) are separated from air (stream 11). The burner or mixer promotes a thorough mixing of the three gas streams in the upper half of the vessel, where the greater part of the partial oxidation takes place very rapidly. The hot gases then pass over into a reforming catalyst, which is located in the bottom half of the vessel where reforming of the natural gas is completed. The catalytic partial oxidation is typically characterized here by the following five chemical reactions:

$$CH_4 + H_2O \rightarrow CO + 3H_2$$

$$CH4 + 2O_2 \rightarrow CO_2 + 2H_2O$$

$$2CO + O_2 \rightarrow 2CO_2$$

$$2H_2 + O_2 \rightarrow 2H_2O$$

$$CO_2 + H_2 = CO + H_2O$$

Steam is admitted to the natural gas (stream 1) in order to achieve a mole ratio of non-oxidized carbon in the natural gas in the range between 1.0 and 3.0 and normally at 1.7 for high pressure operation. Oxygen is admitted to the CPOX reactor in a mole ratio to non-oxidized carbon of between 0.45 and 0.7, usually 0.52. The amount of oxygen is in practice precisely controlled in order to hold the outlet temperature from the CPOX reactor to between 900° C. and 1050° C., and normally 960° C. The purity of the oxygen (stream 13), which is produced from the air separation unit G, lies between 90% and 99.5%, and is generally 99.5%. The catalyst that is typically utilized in the CPOX reactor is a nickel oxide catalyst, for example from Type G-31E, G9OLDP and G-90B from the firm Süd-Chemie. The pressure at which the catalytic partial oxidation reaction takes place is between 25 bar and 100 bar, and normally 40 bar.

Another possibility for production of synthesis gas in reactor A comprises the combination of a steam reformer with the CPOX reactor. Thereby a part of the natural gas is fed to the steam reformer in which, at temperatures between 700° C. and 950° C., preferably at 780° C. in a mole ratio of steam to carbon between 1.5 and 3.0, preferably 2.0 and at a pressure between 25 and 50 bar, preferably at 40 bar, it is converted catalytically to synthesis gas in accordance with the following reaction equations:

$$CH_4 + H_2O \rightarrow CO + 3H_2$$

$$CO_2 + H_2 \rightarrow CO + H_2O$$

Typically a nickel/aluminum oxide catalyst is employed for this, for example Typ G-9OLDP or G-90B from the firm SüdChemie.

Subsequently, the reformed natural gas is mixed with the portion of the natural gas stream which is fed in a bypass around the steam reformer, and into the CPOX reactor.

Alternatively, dividing the natural gas stream can be foregone, in that the entire natural gas-stream is first fed through the steam reformer and then through the CPOX reactor.

The combination of a steam reformer with a CPOX reactor, especially the method by which the natural gas is quantitatively divided between the steam reformer and the CPOX reactor, enhances the flexibility of the entire method relative to the gas composition.

In reactor B the carbon monoxide present in the gas mixture is converted to carbon dioxide in a one or two stage catalytic converter, wherein between the stages cooling, and behind the reactor B a further cooling of stream 4 are provided, and resulting from that heat recovery. The catalyzer can comprise a one or more beds of known high temperature conversion catalysts and also at least one bed of the likewise known low temperature conversion catalysts.

In the compressor and absorber C, the raw gas is if necessary compressed at increased pressure, and the carbon dioxide is removed from the gas. The removal of carbon dioxide from the raw synthesis gas is carried out with an absorbent either by means of a physical washing or a chemical washing. In the case of a physical washing the absorbent is typically cold methanol or glycolether. In the case of a chemical washing, the absorbent is typically an alkanolamine, a polyalkanolamine or potassium carbonate. In the absorber the carbon dioxide in the raw synthesis gas is removed to a content of less than 50 ppmv, generally even less than 10 ppmv. The pressure at which the carbon dioxide is removed, is 30 bar to 100 bar, normally at 80 bar. The compressor and absorber C includes a device for controlled lowering of the pressure for the absorbent for recovering carbon dioxide, a device for the regeneration of absorbent by heat input, also a device for maintenance of the correct composition of absorbent and finally a device for the renewed admission of solvent pressure to the level of the process pressure. The entire amount of carbon dioxide recovered or parts thereof can be separated and used for example for a urea synthesis (stream 14). Unused carbon dioxide is released into the atmosphere.

Remaining impurities in the synthesis gas such as methane, traces of carbon monoxide and argon are washed out in the purification unit D with for example liquid nitrogen by means of a molecular sieve generally known as variable pressure absorption. The products of purification unit D are a pure stream for ammonia synthesis gas, which in the case of washing with liquid nitrogen exhibits the correct stoichiometric ratio, and by application of variable pressure absorption a pure stream of hydrogen. In both cases a stream of all remaining impurities is used as fuel gas for the process ovens. The pressure at which the purification unit is operated lies between 30 bar and 100 bar, and normally at 75 bar when washing with liquid nitrogen and 30 bar for application of variable pressure absorption. If the purification unit comprises washing with liquid nitrogen, then a molecular sieve installation for removal of traces of carbon dioxide and an absorbent connected upstream in the carbon dioxide-free synthesis gas.

In the unit E the methanol synthesis gas (stream 7) is converted by means of a catalyst into methanol and the methanol refined (stream 9) by distillation to the required purity. The pressure at which methanol synthesis takes place is between 60 and 120 bar, normally at 70 bar. The distillation of methanol takes place between approximately 15 bar and atmospheric pressure.

In unit F the ammonia synthesis gas (stream 8) is compressed and is converted by a catalyst into ammonia (stream 10).

The ammonia is separated from recovered synthesis gas by partial condensation at low temperatures, wherein liquid ammonia is used as cooling means. The pressure, at which the ammonia synthesis takes place is between 120 and 250 bar, and normally at 200 bar.

In the air separation unit G the components oxygen (stream 13) and nitrogen (stream 12) are separated sequentially from the air by low temperature distillation. The process of air splitting into its components is well-known. The products from the air separation unit G comprise an oxygen stream having a purity between 90% and 99.5%, normally at 99.5%, a nitrogen stream with a purity of more than 99.995% and a waste gas stream with the waste products oxygen and nitrogen which are normally released into the atmosphere. The air separation unit G can also, if one wishes, produce s a stream one or more of the rare gases such as argon, helium and neon.

The invention claimed is:

1. A method for coproducing methanol and ammonia from natural gas, which comprises the steps of:
   (a) mixing natural gas, steam and oxygen which has a purity of 90 to 99.5% in a catalytic partial oxidation reactor in the presence of a catalyst for reforming natural gas to partially oxidize and reform the natural gas into a gas mixture which comprises carbon monoxide, carbon dioxide, hydrogen and steam;
   (b) dividing the gas mixture obtained in step (a) into two portions, a larger portion for hydrogen production and a smaller portion for methanol synthesis;
   (c) catalytically converting the carbon monoxide in the larger portion of the gas mixture for hydrogen production to carbon dioxide to obtain a gas mixture rich in hydrogen and carbon dioxide in a one or two stage catalytic converter, and cooling the gas mixture rich in hydrogen and carbon dioxide thus produced;
   (d) passing the gas mixture rich in hydrogen and carbon dioxide to a purification unit having a molecular sieve and maintained at a pressure of 30 to 100 bar, passing the gas mixture rich in hydrogen and carbon dioxide through the molecular sieve using variable pressure absorption, to separate the carbon dioxide from the hydrogen, splitting the hydrogen into two streams, combining one stream of hydrogen with the smaller portion of the gas mixture obtained in step (b) for synthesis of methanol, and subsequently washing out any residual impurities from the other stream of hydrogen , including methane, carbon monoxide, and argon, with a stream of liquid nitrogen to obtain a pure stream of hydrogen and nitrogen for ammonia synthesis, and returning the washed out residual impurities as a fuel to the catalytic partial oxidation reactor according to step (a);
   (e) catalytically converting the smaller portion of the gas mixture obtained in step (b) combined with the stream of hydrogen according to step (d) to methanol, and purifying the methanol by distilling the methanol at a pressure between atmospheric pressure and 15 bar; and
   (f) catalytically converting the pure stream of hydrogen and nitrogen obtained according to step (d) to ammonia, and separating the ammonia by means of partial condensation.

2. The process defined in claim 1, wherein according to step (a) a part of the natural gas is first fed through a steam reformer, in which at a temperature between 700 and 950° C., in a molar ratio of steam to carbon between 1.5 and 3.0, and at a pressure between 25 and 50 bar, the natural gas is catalytically converted to synthesis gas, and the synthesis gas is subsequently mixed with additional natural gas and fed into the catalytic partial oxidation reactor.

3. A method for coproducing methanol and ammonia from natural gas, which comprises the steps of:
   (a) mixing natural gas, steam and oxygen which has a purity of 90 to 99.5% in a catalytic partial oxidation reactor in the presence of a catalyst for reforming natural gas to partially oxidize and reform the natural gas into a gas mixture which comprises carbon monoxide, carbon dioxide, hydrogen and steam;
   (b) dividing the gas mixture obtained in step (a) into two portions, a larger portion for hydrogen production and a smaller portion for methanol synthesis;
   (c) catalytically converting the carbon monoxide in the larger portion of the gas mixture for hydrogen production to carbon dioxide to obtain a gas mixture rich in hydrogen and carbon dioxide in a one or two stage catalytic converter, and cooling the gas mixture rich in hydrogen and carbon dioxide thus produced;
   (d) passing the gas mixture rich in hydrogen and carbon dioxide to a carbon dioxide absorption column, and the carbon dioxide is washed out of the gas mixture to yield a gas mixture rich in hydrogen;
   (e) passing the gas mixture rich in hydrogen to a purification unit having a molecular sieve and maintained at a pressure of 30 to 100 bar, splitting the hydrogen into two streams combining one stream of hydrogen with the smaller portion of the gas mixture obtained in step (b) for synthesis of methanol, and subsequently washing out any residual impurities from the other stream of hydrogen, including methane, carbon monoxide, and argon, with a stream of liquid nitrogen, to obtain a pure stream of hydrogen and nitrogen for ammonia synthesis and returning the washed out residual impurities as a fuel to the catalytic partial oxidation reactor according to step (a);
   (f) catalytically converting the smaller portion of the gas mixture obtained in step (b) combined with the stream of hydrogen according to step (e) to methanol , and purifying the methanol by distilling the methanol at a pressure between atmospheric pressure and 15 bar; and
   (g) catalytically converting the pure stream of hydrogen and nitrogen obtained according to step (e) to ammonia, and separating the ammonia by means of partial condensation.

4. The process defined in claim 3, wherein according to step (a) a part of the natural gas is first fed through a steam reformer, in which at a temperature between 700 and 950° C., in a molar ratio of steam to carbon between 1.5 and 3.0, and at a pressure between 25 and 50 bar, the natural gas is catalytically converted to synthesis gas, and the synthesis gas is subsequently mixed with additional natural gas and fed into the catalytic partial oxidation reactor.

5. The process defined in claim 3, wherein according to step (d), the gas mixture rich in hydrogen and carbon dioxide is compressed to aid in removing carbon dioxide from the gas mixture.

6. The process defined in claim 5, wherein the gas mixture rich in hydrogen and carbon dioxide is washed with the help of a physical absorbent.

7. The process defined in claim 6 wherein the physical absorbent is selected from the group consisting of cold methanol and glycolether.

8. The process defined in claim 5, wherein the gas mixture rich in hydrogen and carbon dioxide is washed with the help of a chemical absorbent.

9. The process defined in claim 8 wherein the chemical absorbent is selected from the group consisting of an alkanolamine, a polyalkanolamine, and potassium carbonate.

10. The process defined in claim 3, wherein according to step (d) the carbon dioxide washed out of the gas mixture is used for urea manufacture.

11. A method for coproducing methanol and ammonia from natural gas, which comprises the steps of:
   (a) mixing natural gas, steam and oxygen which has a purity of 90 to 99.5% in a catalytic partial oxidation reactor in the presence of a catalyst for reforming natural gas to partially oxidize and reform the natural gas into a gas mixture which comprises carbon monoxide, carbon dioxide, hydrogen and steam;
   (b) dividing the gas mixture obtained in step (a) into two portions, a larger portion for hydrogen production and a smaller portion for methanol synthesis;
   (c) catalytically converting the carbon monoxide in the larger portion of the gas mixture for hydrogen production to carbon dioxide to obtain a gas mixture rich in hydrogen and carbon dioxide in a one or two stage catalytic converter, and cooling the gas mixture rich in hydrogen and carbon dioxide thus produced;
   (d) passing the gas mixture rich in hydrogen and carbon dioxide to a carbon dioxide absorption column, washing out the carbon dioxide of the gas mixture to yield a gas mixture rich in hydrogen, splitting the hydrogen into two streams combining one stream of hydrogen with the smaller portion of the gas mixture obtained in step (b) for synthesis of methanol, and introducing the other stream of hydrogen into a purification unit having a molecular sieve and maintained at a pressure of 30 to 100 bar for subsequent ammonia synthesis;
   (e) further introducing into the purification unit, a stream of liquid nitrogen for washing out any residual impurities from the other stream of hydrogen, including methane, carbon monoxide, and argon, to obtain a pure stream of hydrogen and nitrogen for ammonia synthesis and returning the washed out residual impurities as a fuel to the catalytic partial oxidation reactor according to step (a);
   (f) catalytically converting the smaller portion of the gas mixture obtained in step (b) combined with the stream of hydrogen according to step (d) to methanol, and purifying the methanol by distilling the methanol at a pressure between atmospheric pressure and 15 bar; and
   (g) catalytically converting the pure stream of hydrogen and nitrogen obtained according to step (e) to ammonia, and separating the ammonia by means of partial condensation.

12. The process defined in claim 11, wherein according to step (a) a part of the natural gas is first fed through a steam reformer, in which at a temperature between 700 and 950° C., in a molar ratio of steam to carbon between 1.5 and 3.0, and at a pressure between 25 and 50 bar, the natural gas is catalytically converted to synthesis gas, and the synthesis gas is subsequently mixed with additional natural gas and fed into the catalytic partial oxidation reactor.

13. The process defined in claim 11, wherein according to step (d), the gas mixture rich in hydrogen and carbon dioxide is compressed to aid in removing carbon dioxide from the gas mixture.

14. The process defined in claim 13, wherein the gas mixture rich in hydrogen and carbon dioxide is washed with the help of a physical absorbent.

15. The process defined in claim 14 wherein the physical absorbent is selected from the group consisting of cold methanol and glycolether.

16. The process defined in claim 11, wherein according to step (d) the gas mixture rich in hydrogen and carbon dioxide is washed with the help of a chemical absorbent.

17. The process defined in claim 16 wherein the chemical absorbent is selected from the group consisting of an alkanolamine, a polyalkanolamine, and potassium carbonate.

18. The process defined in claim 11, wherein according to step (d) the carbon dioxide washed out of the gas mixture is used for urea manufacture.

* * * * *